(12) United States Patent
Garrett et al.

(10) Patent No.: US 7,674,622 B2
(45) Date of Patent: Mar. 9, 2010

(54) METHOD FOR DETERMINATION OF NUCLEATED RED BLOOD CELLS AND LEUKOCYTES IN A WHOLE BLOOD SAMPLE IN AN AUTOMATED HEMATOLOGY ANALYZER

(75) Inventors: Diana G. Garrett, Scotts Valley, CA (US); Hyejung C. Lee, Gilroy, CA (US); Show-Chu Wong, Sunnyvale, CA (US); Bodo Roemer, Saulheim (DE); Sherb M. Edmondson, Jr., Sunnyvale, CA (US)

(73) Assignee: Abbott Laboratories, Inc., Abbott Park, IL (US)

( * ) Notice: Subject to any disclaimer, the term of this patent is extended or adjusted under 35 U.S.C. 154(b) by 89 days.

(21) Appl. No.: 11/644,318

(22) Filed: Dec. 22, 2006

(65) Prior Publication Data

US 2008/0153170 A1    Jun. 26, 2008

(51) Int. Cl.
*G01N 33/48* (2006.01)
*G01N 21/00* (2006.01)

(52) U.S. Cl. .............. 436/10; 436/8; 436/17; 436/63; 436/164; 436/174; 436/175; 422/73; 422/82.05; 422/82.09; 435/2

(58) Field of Classification Search .......... 436/8, 436/10, 17, 18, 63, 164, 174, 175; 422/73, 422/82.05, 82.09; 435/2
See application file for complete search history.

(56) References Cited

U.S. PATENT DOCUMENTS

| | | | |
|---|---|---|---|
| 4,284,412 A | 8/1981 | Hansen et al. | |
| 5,039,613 A | 8/1991 | Matsuda et al. | |
| 5,227,304 A | 7/1993 | Wong | |
| 5,387,633 A | 2/1995 | Bush et al. | |
| 5,510,267 A | 4/1996 | Marshall | |
| 5,559,037 A | 9/1996 | Kim et al. | |
| 5,631,165 A | 5/1997 | Chupp et al. | |
| 5,648,225 A * | 7/1997 | Kim et al. | 435/7.24 |
| 5,874,310 A | 2/1999 | Li et al. | |
| 5,879,900 A | 3/1999 | Kim et al. | |
| 5,917,584 A | 6/1999 | Li et al. | |
| 5,958,781 A * | 9/1999 | Wong et al. | 436/63 |
| 6,228,652 B1 | 5/2001 | Rodriguez et al. | |
| 6,410,330 B1 * | 6/2002 | Li et al. | 436/10 |
| 6,472,215 B1 | 10/2002 | Huo et al. | |
| 6,573,102 B2 | 6/2003 | Li et al. | |
| 6,630,990 B2 * | 10/2003 | van't Oever et al. | 356/39 |
| 6,740,527 B1 | 5/2004 | Wong et al. | |
| 6,890,756 B2 * | 5/2005 | Wu | 436/66 |
| 7,008,792 B2 * | 3/2006 | Lopez et al. | 436/10 |
| 7,208,319 B2 * | 4/2007 | Lopez et al. | 436/10 |
| 2004/0209377 A1 | 10/2004 | Crews et al. | |
| 2006/0203226 A1 | 9/2006 | Roche et al. | |

FOREIGN PATENT DOCUMENTS

EP    0582736 A1    2/1994

OTHER PUBLICATIONS

European Patent Office, International Search Report, Mar. 27, 2008.

* cited by examiner

*Primary Examiner*—Maureen M Wallenhorst
(74) *Attorney, Agent, or Firm*—David L. Weinstein

(57) ABSTRACT

A method for enumerating white blood cells and nucleated red blood cells. The steps of the method are as follows:
(a) providing a lysed sample of whole blood;
(b) introducing the lysed sample to a light-scattering multi-angle depolarizing flow cytometer;
(c) removing depolarizing interference, e.g., lipid droplets and other measured particles;
(d) differentiating nucleated red blood cells and noise from white blood cells in the absence of depolarizing interference;
(e) differentiating nucleated red blood cells from noise in the absence of depolarizing interference and white blood cells; and
(f) differentiating possible platelet clumps.

8 Claims, 13 Drawing Sheets

METHOD FOR DETERMINATION OF NUCLEATED RED BLOOD CELLS AND LEUKOCYTES IN A WHOLE BLOOD SAMPLE IN AN AUTOMATED HEMATOLOGY ANALYZER

BACKGROUND OF THE INVENTION

1. Field of the Invention

This invention relates to a method for the determination of leukocytes in samples of whole blood. More particularly, this invention relates to a method of distinguishing nucleated red blood cells from leukocytes, thereby enabling more accurate complete blood counts.

2. Discussion of the Art

One of the most important clinical results produced by an automated hematology analyzer is the concentration of white blood cells. Nucleated red blood cells tend to interfere with white blood cells, thereby causing the analyzer to either flag the white blood cell counting, thereby rendering the concentration of white blood cells not reportable, or including the nucleated red blood cells in the white blood cell count, thereby producing an inaccurate result. Specimens containing fragile white blood cells or specimens containing hypotonically resistant red blood cells present a problem for automated hematology analyzers. Fragile white blood cells can be lysed along with red blood cells, thereby rendering the white blood cell count inaccurate as being too low. Hypotonically resistant red blood cells, which resist lysing, can be counted as white blood cells, thereby rendering the white blood cell count inaccurate as being too high. Hematology analyzers invalidate these inaccurate results, with the result that the operator is forced to acquire a reportable result by manual means.

Red blood cells are produced from bone marrow progenitors through a programmed series of intermediate developmental stages. All of the precursors of red blood cells are nucleated and are normally located within the bone marrow. As these precursors mature toward the erythrocyte stage, there are progressive decreases in RNA/DNA synthesis and an increase in hemoglobin content. Although nucleated red blood cells may occur as rare events in the blood of normal adults, their frequency is so low that, when seen, they are regarded as a significant abnormality.

The presence of nucleated red blood cells in the blood usually provides valuable insights into the cause of a variety of hematological disorders. When nucleated red blood cells are present in a blood sample, there is a need to ensure that they do not interfere with the white blood cell counting.

Interference of white blood cell counting by nucleated red blood cells generally adversely affect the accuracy of the method and, consequently, the performance of a hematology analyzer for the complete blood count. Historically, this adverse effect has required morphological assessment of the nucleated red blood cell count, along with subsequent correction of the reported leukocyte counts. More recently, however, application of fluorescence flow cytometry has resulted in the development of semi-automated methods and fully automated nucleated red blood cell counting performed as part of the complete blood count.

Manual nucleated red blood cell counting remains the reference method. Manual nucleated red blood cell counting calls for the use of 200 or 100 leukocyte differentials. Despite the fact that accuracy of nucleated red blood cell recognition is high, it is clear that the statistical limitations of the 100 or 200 leukocyte differentials result in apparent inaccuracy and insensitivity when the ratio of nucleated red blood cells to white blood cells is below about 10%. While fluorescence flow cytometry techniques can accurately resolve nucleated red blood cells from other cellular components of the blood, in practice, the expense of these procedures as well as their reliance on many manual intervention steps, prevent widespread application for routine clinical uses.

The nucleated red blood cell count is usually calculated from the ratio of nucleated red blood cell count to the total white blood cell count, or mean nucleated red blood cell count per 100 white blood cells. In a whole blood sample, when nucleated red blood cells are present, there are often other blood components, such as hypotonically resistant red blood cells, platelet clumps, and cell debris to interfere with the nucleated red blood cell count. Those interfering substances are often critical factors, or limitations, of the method to determine the performance or quality of nucleated red blood cell count and white blood cell count for the complete blood count (CBC).

Several automated hematology systems offer nucleated red blood cell estimation as an integral part of the complete blood count. Many automated hematology systems comprise a flow cytometer that has been specifically designed for complete blood count in addition to performing some automated fluorescence flow cytometry techniques. The systems are capable of simultaneously performing a leukocyte differential and nucleated red blood cell analysis. However, some samples from newborn babies, sickle, and thalassemic red blood cells and nucleated red blood cells are resistant to the lytic reagents used during analysis of nucleated red blood cells. These samples often give an incorrect nucleated red blood cell count or an incorrect white blood cell count or both an incorrect nucleated red blood cell count and an incorrect white blood cell count. In order to solve this problem, an extra step is needed to prolong incubation time for lysing most of the hypotonically resistant red blood cells and nucleated red blood cells. However, during any lysing process, it is possible to lyse some of the small or fragile lymphocytes, which may then be misclassified as nucleated red blood cells. In addition, fluorescent dyes and special reagents for performing some automated fluorescence flow cytometry techniques are costly.

Enumeration of nucleated red blood cells is important because nucleated red blood cells interfere with the white blood cell count. Interference with white blood cell counting is a serious problem because users do not have another way to count white blood cells. When instruments invalidate the white blood cells, users need to use another instrument to determine the white blood cell count. Before the advent of automated hematology analyzers, a manual count performed by viewing a grid on a slide was the only way to determine a white blood cell count.

It would be desirable to develop a cost effective, simple, and reliable method for determining nucleated red blood cells, especially for samples that contain hypotonically resistant red blood cells, which frequently contain nucleated red blood cells.

SUMMARY OF THE INVENTION

The method of this invention is capable of using a combination of a particular lyse reagent with a light scattering, multi-angle depolarizing flow cytometer to determine both the concentration of nucleated red blood cells and the concentration of white blood cells. The method involves separating the population of nucleated red blood cells from the population of white blood cells and identifying other interfering particles, such as, for example, platelet clumps, lipids, and lysed red blood cells in particulate form.

In one aspect, this invention provides a method for enumeration of nucleated red blood cells and white blood cells from the same aliquot of sample used for the determination of hemoglobin. The invention employs a combination of a lyse reagent with light scattering, multi-angle depolarizing flow cytometer. The method of this invention comprises the steps of:

(a) providing a lysed sample of whole blood;
(b) introducing the lysed sample to a light-scattering multi-angle depolarizing flow cytometer;
(c) removing depolarizing interference, e.g., lipid droplets and other measured particles;
(d) differentiating nucleated red blood cells and noise from white blood cells in the absence of depolarizing interference;
(e) differentiating nucleated red blood cells from noise in the absence of depolarizing interference and white blood cells; and
(f) differentiating possible platelet clumps.

A light-scattering multi-angle depolarizing flow cytometer suitable for use in the method of this invention requires the following detectors: 0°, 10°, 90°, 90° Depolarized for removing interference. The lyse reagent is preferably a three part differential cyanide-free lyse reagent that enables the nuclei to remain intact while lysing hypotonically resistant red blood cells.

The method of this invention reduces interference from hypotonically resistant red blood cells, fragile white blood cells, platelet clumps, lipids, reticulocytes, and cell debris in clinical blood samples. In addition, the method of this invention can be used to analyze bone marrow samples and cord blood samples, which tend to have many interfering substances. The invention makes it possible to perform accurate total white blood cell and nucleated red blood cell counts, and detection and enumeration of platelet clumps in the same blood sample with the same lyse reagent in a single dilution of a blood sample. In addition, the enumeration of all nucleated cells enables a more accurate correction for absorbance interference of hemoglobin measurements when high numbers of nuclei (white blood cells or nucleated red blood cells) are present. The method of this invention provides a simple, cost-effective, and reliable fully automated hematology method for enumeration of nucleated red blood cells and white blood cells.

Other methods of the prior art are not able to perform accurate total white blood cell and nucleated red blood cell counts when interfering substances, such as, for example, hypotonically resistant red blood cells, platelet clumps, lipids, etc., are present in the clinical blood samples.

DETAILED DESCRIPTION

Figure 1A:
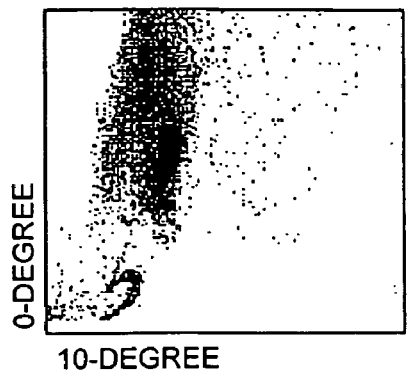
FIG. 1A is a scatter plot that illustrates 10°/0° scattering for removal of depolarizing interference.

As used herein, the expression "morphological assessment" means assessment of the shape of a cell. The term "leukocyte" means white blood cell. Unlike red blood cells, white blood cells occur in many different types. Examples of leukocytes include granulocytes, neutrophils, eosinophils, basophils, lymphocytes, and monocytes. The expression "reference method" means a method of the prior art against which a test method is compared. The term "sickle cell" means a red blood cell shaped like a sickle. A sickle cell is typically resistant to a lyse reagent. The term "thalassemic" relates to a genetic blood disorder in which the bone marrow cannot form sufficient red cells and red cell survival is also reduced. The term "lymphocyte" means a white blood cell that matures in lymph nodes, the spleen, and other lymphoid tissues, enters the blood, and circulates throughout the body. The expression "nucleated red blood cell" means an immature red blood cell that still contains a nucleus. As used herein, the term "noise" includes, but is not limited to, such substances as lysed red blood cells in particulate form, cell debris, and platelet clumps.

As used herein, the term "event" means a particle of that is of a size sufficient to trigger the 0° detector, whereby that detector signals the analyzer to collect 0°, 10°, 90°, and 90° depolarized measurements of that particle. Particles include, but are not limited to, are white blood cells (WBC), red blood cells (RBC), platelets (PLT), RBC fragments, WBC fragments, lipids, platelet (PLT) clumps.

As used herein, the expression "lyse reagent" means a lyse reagent of the type described in U.S. Pat. No. 5,958,781, incorporated herein by reference. As used herein, the term "diluent" means a diluent of the type described in U.S. Pat. No. 5,227,304, incorporated herein by reference.

The method of this invention can be performed with an automated hematology analyzer having a laser light source with a multi-directional detection system, a multi-angle depolarizing flow cytometer, such as, for example, a cytometer of the type described in U.S. Pat. No. 5,510,267, incorporated herein by reference. A representative example of a commercially available automated hematology analyzer suitable for use in the method of this invention is a CELL-DYN® 3000 Series analyzer using a red laser light source, commercially available from Abbott Laboratories, Abbott Park, Ill. Detection of optical scattering at 0° and 10° are preferred for detection and measurement of total white blood cell and nucleated red blood cell counts. Prior to being analyzed by the flow cytometer, the blood sample to be analyzed is subjected to a differential lyse reagent. A representative example of a commercially available differential lyse reagent suitable for use in the method of this invention is described in U.S. Pat. No. 5,958,781, previously incorporated herein by reference.

A schematic diagram of an automated hematology analyzer suitable for use in this invention can be found in U.S. Pat. No. 5,510,267, previously incorporated herein by reference. U.S. Pat. No. 5,510,267 also describes in detail the principle of impedance cell counting and sizing. U.S. Pat. No. 5,510,267 further describes an optical transducer suitable for use with the automated hematology analyzer that can be used to practice this invention.

The type of lyse reagent and the concentration thereof are important for the method of this invention. The method of this invention calls for the use of a lysed sample. In one embodiment, the sample can be lysed by mixing a lyse reagent (such as, for example, the lyse reagent described in U.S. Pat. No. 5,958,781) with a sample diluted with a diluent (such as, for example, the diluent described in U.S. Pat. No. 5,227,304). The ratio of the lyse reagent to the diluent can range from about 1:3 to about 1:8. The lysing reagent lyses the whole blood sample to form a lysate. A portion of the lysate is transferred to a hemoglobin flow cell for hemoglobin measurement (as described in U.S. Pat. No. 5,958,781), and then the remaining portion of the lysate or the lysate previously used is transferred to an automated analyzer for counting of white blood cells and nucleated red blood cells. As used herein, the range "from about 1:3 to about 1:8" means about one part lyse reagent to about three to eight parts diluent.

In the preferred embodiment, the lyse reagent comprises an aqueous solution of one or more quaternary ammonium salts (e.g., Br or Cl) in an amount ranging from about 15 to about 150 g/L and hydroxylamine salts (e.g., HCl) in an amount ranging from about 0.5 to about 50 g/L; sodium chloride in an amount ranging from about 0 to about 10 g/L; having a pH of from about 2.5 to about 6.0; and having an osmolality of in an amount ranging from about 150 to about 700 mOsm/kg.

The method of this invention eliminates counting the substances that interfere with the counting of nucleated red blood cells and white blood cells in all clinical blood samples and provides an accurate first pass result with all clinical blood samples, unlike methods of the prior art. Interferences that are omitted using the multi-dimensional algorithm of this invention include:

(1) Lysed red blood cells in particulate form, which are omitted by using data collected by 0° and 10° detectors.
(2) Lipids, which are omitted by using data collected by 90° Depolarized and 0° detectors.
(3) Platelet clumps, which are omitted by using data collected by 90° detector.

The method of this invention can be used with known and reliable apparatus, such as, for example, automated hematology analyzers that are commercially available or are currently being developed, and known and reliable reagents, such as, for example, very low cost reagents for determining white blood cells and hemoglobin.

In particular, the method of this invention can be used with the CELL-DYN® 3000 series of automated hematology analyzers with updated flowscript and software. Furthermore, the method of this invention can be used with CELL-DYN® 4000/Sapphire series of automated hematology analyzers with optical and software improvements.

Eliminating interferences provides:
(1) An increase in first run reportable white blood cells (less invalidation);
(2) Sensitive enumeration of platelet clumps;
(3) Sensitive enumeration of lipid droplets.

In other methods in the art, blood specimens that contain hypotonically resistant red blood cells or fragile white blood cells tend to be problematic. Those methods attempt to produce a white cell differential at the same time as white blood cell counts and nucleated red blood cell counts. The method of this invention differentiates between nucleated red blood cells and white blood cells, whereby hypotonically resistant red blood cells and fragile white blood cells are not problematic. When used with a hematology analyzer, the method of this invention will not require an additional reagent for analysis because the reagent used is already used for determination of hemoglobin. With a more accurate white blood cell count, the correction of determination of hemoglobin for white blood cell count can be improved as well.

The method of this invention enables accurate counting of total white blood cells and nucleated red blood cells with a single blood sample and the same reagent, without significant interference from the hypotonically resistant red blood cells, platelet clumps, reticulocytes, and cell debris that are present. The method of this invention does not significantly affect the white blood cell counts of fragile lymphocytes and other leukocytes in all clinical blood samples. The method of this invention also detects and counts platelet clumps in the same assay, and can be used with bone marrow and cord blood samples without significant interference.

The following non-limiting examples illustrate the method of this invention. In the following examples, the parameters that are measured are described as follows:

(1) 0° light scatter: light scattered at from about 1° to about 3° with respect to the laser beam.
(2) 10° light scatter: light scattered at from about 3° to about 10° with respect to the laser beam.
(3) 90° light scatter: light scattered orthogonally to the laser beam.
(4) 90° depolarized light scatter: light scattered orthogonally to the laser beam, which by interaction with white cells is no longer vertically polarized.

EXAMPLE 1

The current CELL-DYN® 3000 Series analyzer and CELL-DYN® Diff Screen reagents, diluent, and lyse reagent, are used for this method. The diluent was described in U.S. Pat. No. 5,227,304, previously incorporated herein by reference and the lyse reagent was described in U.S. Pat. No. 5,958,781, previously incorporated herein by reference. The method involves the step of mixing lyse reagent with a whole blood sample diluted by a diluent, wherein the ratio lyse reagent to diluent ranges from about 1 part lyse reagent to from about 3 parts to about 8 parts diluent. The lyse reagent lyses the whole blood sample to form a lysate. The lysate is then transferred to the analyzer for white blood cell and nucleated red blood cell counting. During actual operation, 200 µL of lyse reagent diluted with 900 µL of diluent is then immediately mixed with 10 µL of blood/sample in the mixing chamber. After a bubble mixing, the lysate is analyzed automatically in the analyzer.

EXAMPLE 2

Figure 1B:
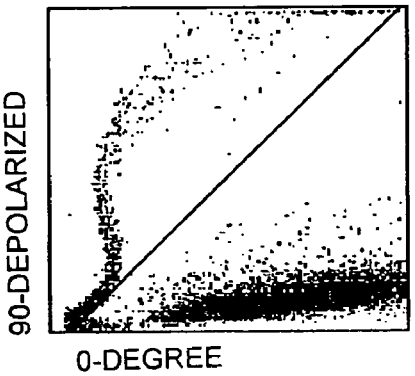
FIG. 1B is a scatter plot that illustrates 0°/90° depolarized scattering for removal of depolarizing interference.
Figure 1C:
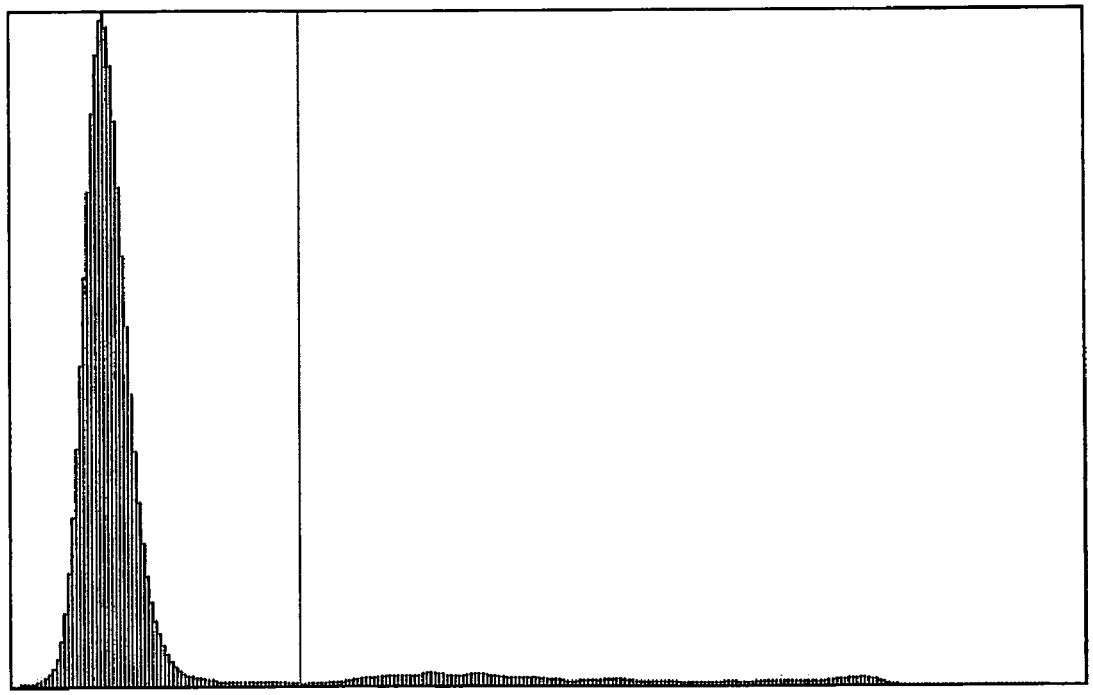
FIG. 1C is a 0°, 90° depolarized histogram that summarizes the results of FIGS. 1A and 1B.

Referring now to FIGS. 1A, 1B, and 1C, with respect to the scatter plot depicting 90° depolarized light scatter versus 0° light scatter for removing depolarizing interference, it can be seen that depolarizing interference is removed because there is a discernible separation between the events above the diagonal line and the events below the diagonal line in FIG. 1B. For each of the scatter plots depicting 90° depolarized light scatter versus 0° light scatter, an imaginary line is drawn to each event from the point x=0, y=0. The angle between the imaginary line and the x-axis is determined for each event. The x-axis of the 0°, 90° depolarizing histogram is divided between the depolarizing events (e.g., lipid events) and the non-depolarizing events (e.g., white blood cell events, nucleated red blood cell events, platelet clump events, and other non-depolarizing substance events).

The 0°, 90° depolarized histogram for removing depolarizing interference shows a high frequency of events to the left of the vertical line and a measurable frequency of events to the right of the vertical line in FIG. 1C. The events to the right of the vertical line in FIG. 1C represent the frequency of the lipid events; the events to the left of the vertical line in FIG. 1C represent the frequency of the remaining events in the samples (e.g., white blood cell events, nucleated red blood cell events, platelet clump events, and other non-depolarizing substance events).

EXAMPLE 3

Figure 2A:
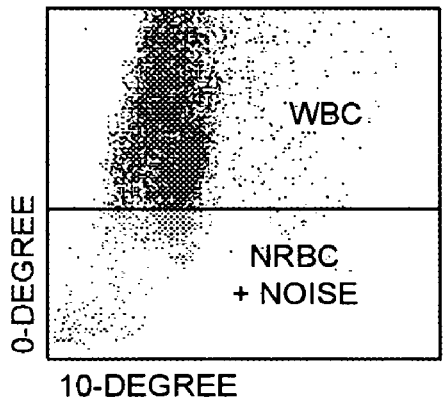
FIG. 2A is a scatter plot that illustrates 10°/0° scattering for differentiating white blood cells and nucleated red blood cells plus noise (lysed red blood cells in particulate form, cell debris, and platelet clumps) in the absence of depolarizing interference.
Figure 2B:
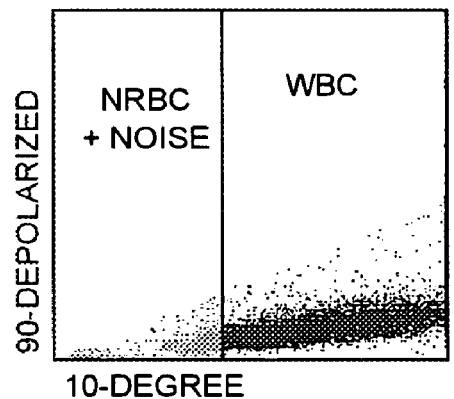
FIG. 2B is a scatter plot that illustrates 10°/90° depolarized scattering for differentiating white blood cells and nucleated red blood cells plus noise (lysed red blood cells in particulate form, cell debris, and platelet clumps) in the absence of depolarizing interference.
Figure 2C:
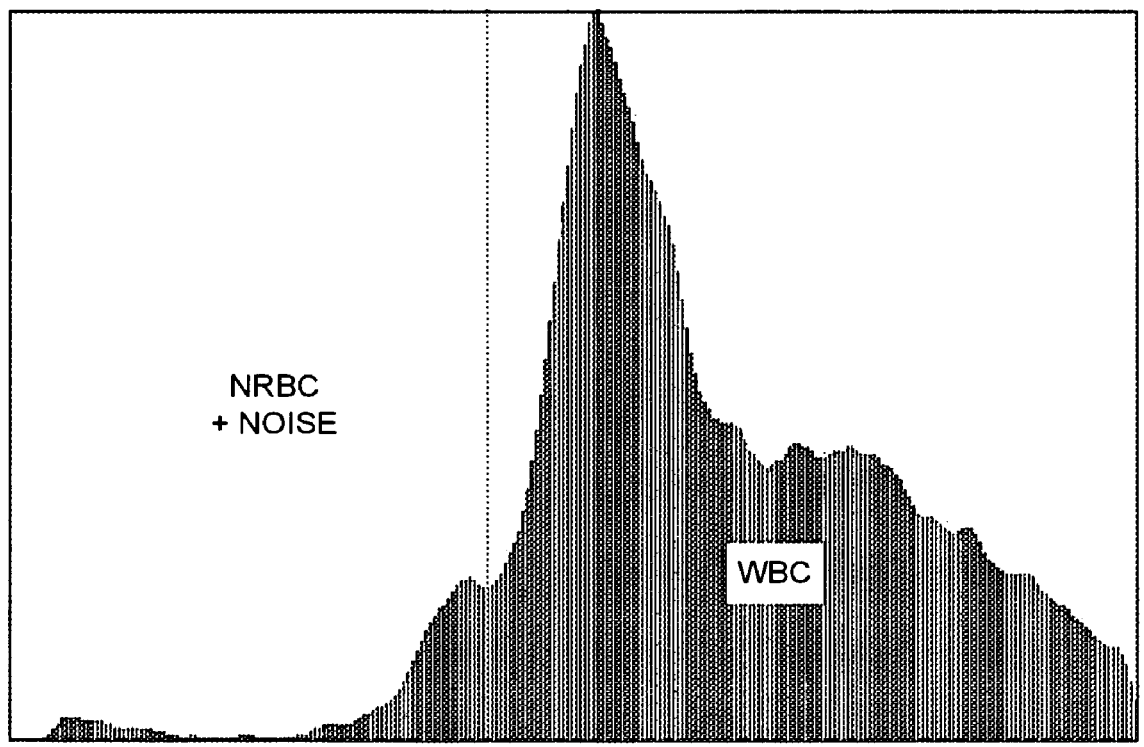
FIG. 2C is a 0° histogram that summarizes the results of FIGS. 2A and 2B.

Referring now to FIGS. 2A, 2B, and 2C, with respect to the differentiation between white blood cells and the combination of nucleated red blood cell events plus noise, it can be seen that there is a high frequency of nucleated red blood cell events plus noise at the bottom of the scatter plot, below the horizontal line in FIG. 2A, depicting 0° light scatter versus 10° light scatter, and a high frequency of white blood cell events at the top of the scatter plot, above the horizontal line in FIG. 2A, depicting 0° light scatter versus 10° light scatter. It can also be seen that there is a high frequency of nucleated red blood cell events plus noise at the left side of the scatter plot, to the left of the vertical line in FIG. 2B, depicting 90° depolarized light scatter versus 0° light scatter, and a high frequency of white blood cell events at the right side of the scatter plot, to the right of the vertical line in FIG. 2B, depicting 90° depolarized light scatter versus 0° light scatter. The 0° histogram in FIG. 2C shows a high frequency of events to the right of the vertical line and a measurable frequency of events to the left of the vertical line in FIG. 2C. The events to the right of the vertical line in FIG. 2C represent the frequency of the white blood cell events; the events to the left of the vertical line in FIG. 2C represent the frequency of the nucleated red blood cell events plus noise.

EXAMPLE 4

Figure 3A:
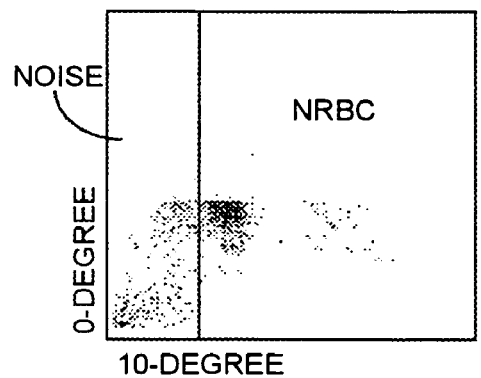
FIG. 3A is a scatter plot that illustrates 10°/0° scattering for differentiating nucleated red blood cells and noise (lysed red blood cells in particulate form, cell debris, and platelet clumps) in the absence of depolarizing interference and white blood cells.
Figure 3B:
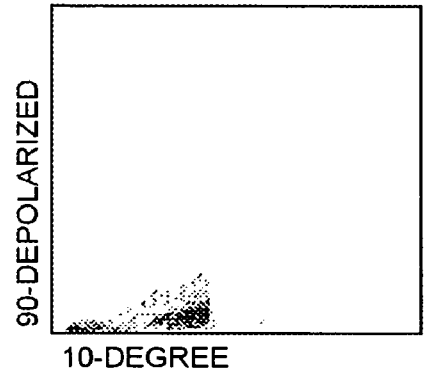
FIG. 3B is a scatter plot that illustrates 10°/90° depolarized scattering for differentiating nucleated red blood cells and noise (lysed red blood cells in particulate form, cell debris, and platelet clumps) in the absence of depolarizing interference and white blood cells.
Figure 3C:
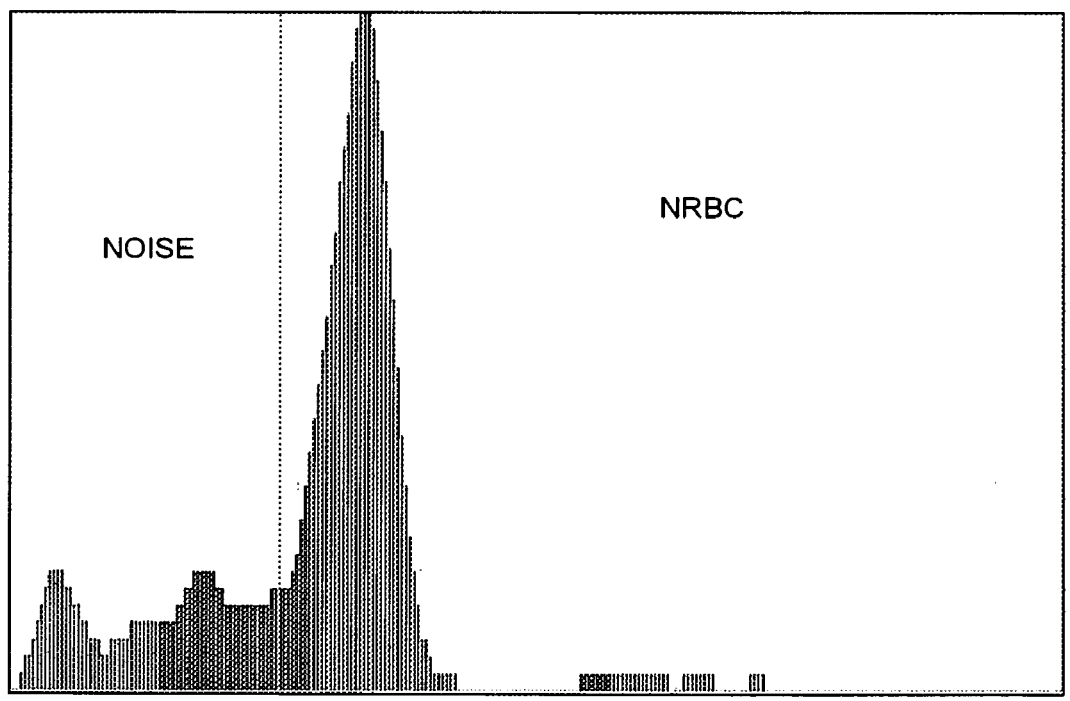
FIG. 3C is a 10° histogram that summarizes the results of FIGS. 3A and 3B.

Referring now to FIGS. 3A, 3B, and 3C, with respect to the differentiation between noise and nucleated red blood cells, it can be seen that there is a high frequency of nucleated red blood cell events at the right side of the scatter plot, to the right of the vertical line in FIG. 3A, depicting 0° light scatter versus 10° light scatter, and a high frequency of noise at the left side of the scatter plot, to the left of the vertical line in FIG. 3A, depicting 0° light scatter versus 10° light scatter. In FIG. 3B, it can be seen that there is a high frequency of nucleated red blood cell events at the bottom of the scatter plot depicting 90° depolarized light scatter versus 10° light scatter. The 10° histogram shows a measurable frequency of events to the left of the vertical line in FIG. 3C and a high frequency of events to the right of the vertical line in FIG. 3C. The events to the right of the vertical line in FIG. 3C represent the frequency of nucleated red blood cell events; the events to the left of the vertical line in FIG. 3C represent the frequency of noise.

EXAMPLE 5

Figure 4A:
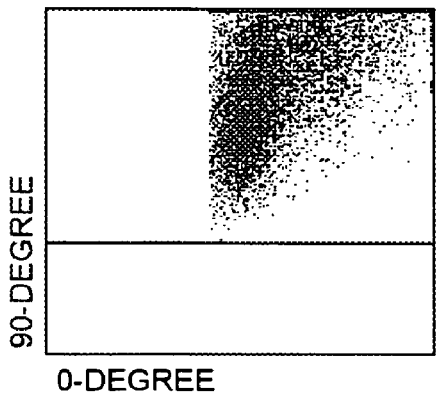
FIG. 4A is a scatter plot that illustrates 0°/90° scattering for differentiating possible platelet clumps and white blood cells.
Figure 4B:
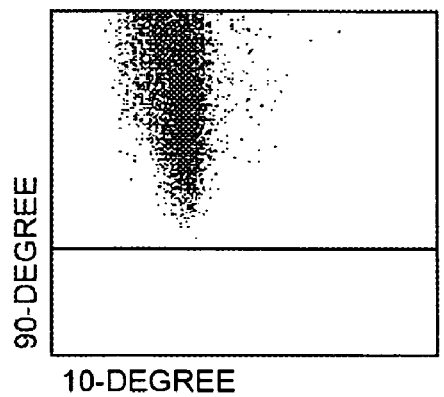
FIG. 4B is a scatter plot that illustrates 10°/90° scattering for differentiating possible platelet clumps and white blood cells.
Figure 4C:
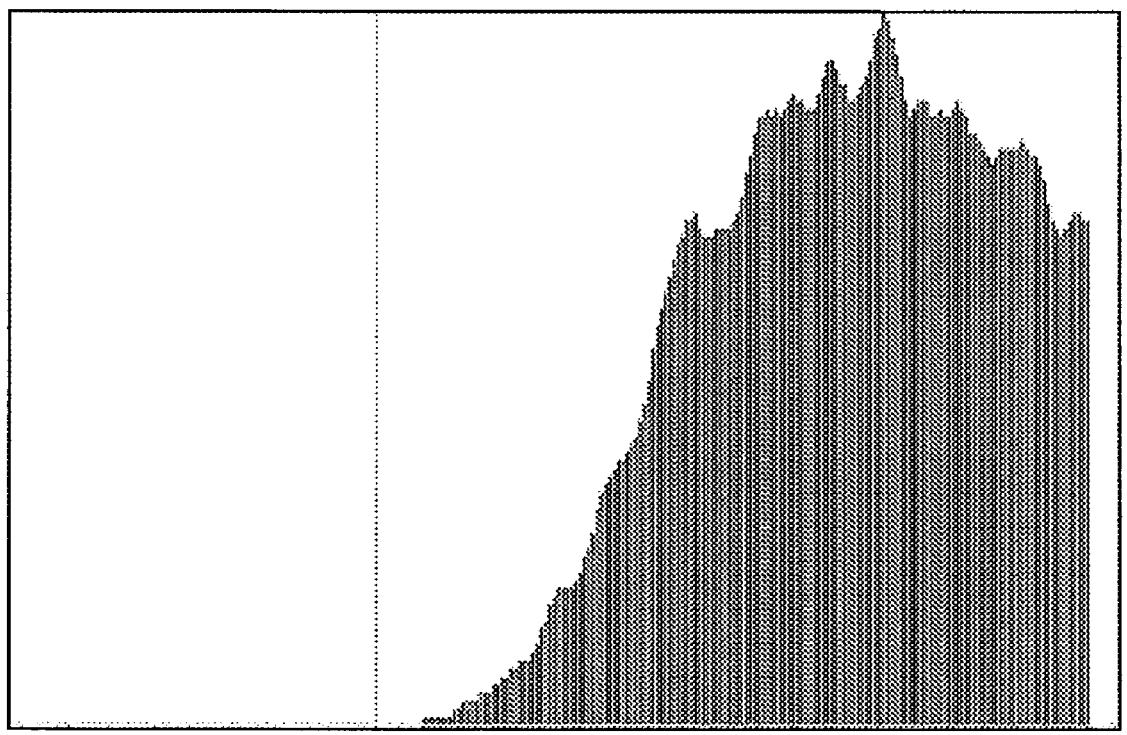
FIG. 4C is 90° a histogram that summarizes the results of FIGS. 4A and 4B.

Referring now to FIGS. 4A, 4B, and 4C, with respect to the differentiation between white blood cells and platelet clumps, it can be seen that there is a high frequency of white blood cell events at the top of the scatter plot, above the horizontal line in FIG. 4A, depicting 90° light scatter versus 0° light scatter, and a low frequency of possible platelet clump events at the bottom of the scatter plot, below the horizontal line in FIG. 4A, depicting 90° light scatter versus 0° light scatter. It can also be seen that there is a high frequency of white blood cell events at the top of the scatter plot, above the horizontal line in FIG. 4B, depicting 90° light scatter versus 10° light scatter, and a low frequency of possible platelet clump events at the bottom of the scatter plot, below the horizontal line in FIG. 4B, depicting 90° light scatter versus 10° light scatter. The 90° histogram shows a non-measurable frequency of events to the left of the vertical line in FIG. 4C and a high frequency of events to the right of the vertical line in FIG. 4C. The events to the right of the vertical line in FIG. 4C represent the frequency of white blood cell events; the events to the left of the vertical line in FIG. 4C represent the possibility of platelet clump events.

From the foregoing examples, EXAMPLES 1 through 5, inclusive, it can be seen that the method of this invention utilizes existing optical equipment and existing reagents in a different way to improve the enumeration of nucleated red blood cells and the enumeration of white blood cells. The existing CELL-DYN® instruments can be set up to focus on particles having the size of nucleated red blood cells. The lyse reagent is optimized to lyse the red blood cells and retain the differentiating properties of the nucleated red blood cells and the white blood cells, thereby improving the sensitivity of existing methods for enumerating nucleated red blood cells and enumerating white blood cells.

EXAMPLE 6

Figure 5A:
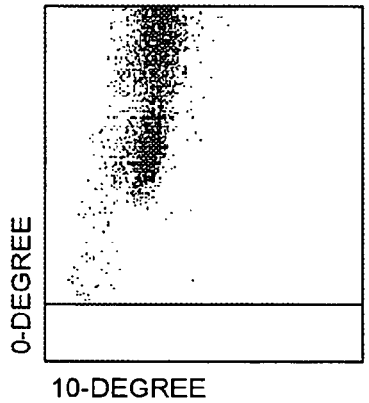
FIG. 5A is a scatter plot that illustrates 10°/0° scattering for determining platelet clumps, without ristocetin.
Figure 5B:
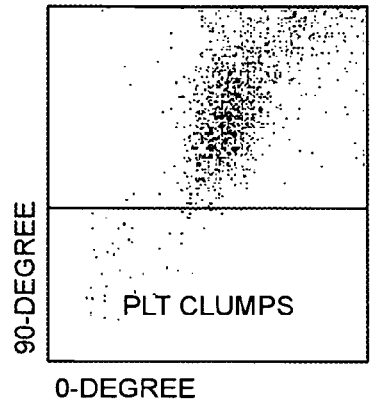
FIG. 5B is a scatter plot that illustrates 0°/90° scattering for determining platelet clumps, without ristocetin.
Figure 5C:
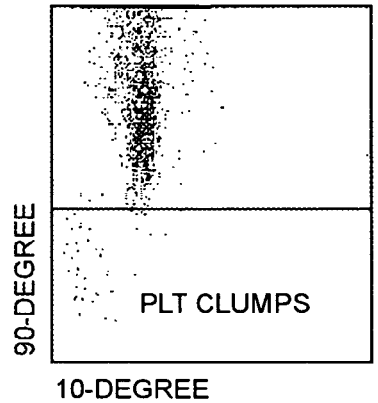
FIG. 5C is a scatter plot that illustrates 10°/90° for determining platelet clumps, without ristocetin.
Figure 5D:
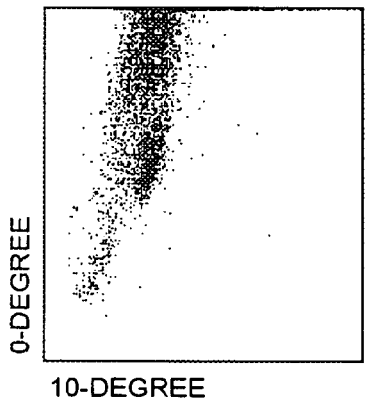
FIG. 5D is a scatter plot that illustrates 10°/90° scattering for determining platelet clumps, with ristocetin.
Figure 5E:
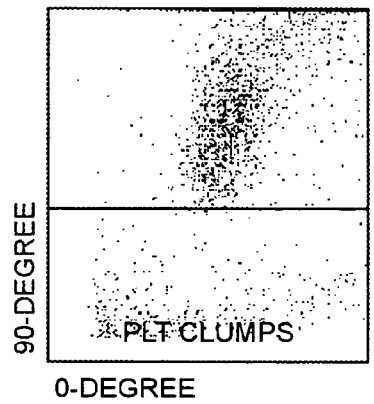
FIG. 5E is a scatter plot that illustrates 0°/90° scattering for determining platelet clumps, with ristocetin.
Figure 5F:
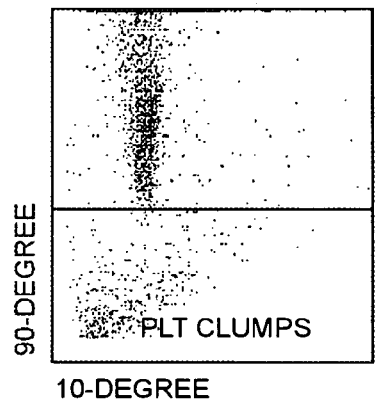
FIG. 5F is a scatter plot that illustrates 10°/90° for determining platelet clumps, with ristocetin.

This example illustrates the differentiation between platelet clumps and white blood cells. Ristocetin is a reagent that can be used to cause platelets to aggregate (clump), whereby detection of the platelets is facilitated. FIG. 5A depicts 0° light scatter versus 10° light scatter; FIG. 5B depicts 90° light scatter versus 0° light scatter; FIG. 5C depicts 90° light scatter versus 10° light scatter. In FIGS. 5A, 5B, and 5C, where ristocetin was not used, the portions above the horizontal lines in FIGS. 5A, 5B, and 5C show white blood cell events. The portions below the horizontal lines in FIGS. 5A, 5B, and 5C show possible platelet clump events. FIG. 5D depicts 0° light scatter versus 10° light scatter; FIG. 5E depicts 90° light scatter versus 0° light scatter; FIG. 5F depicts 90° light scatter versus 10° light scatter. In FIGS. 5E and 5F, where ristocetin was used, the portions above the horizontal lines show white blood cell events. The portions below the horizontal lines show possible platelet clump events. It can be seen that the employment of ristocetin enables detection of platelet clumps.

Figure 6A:
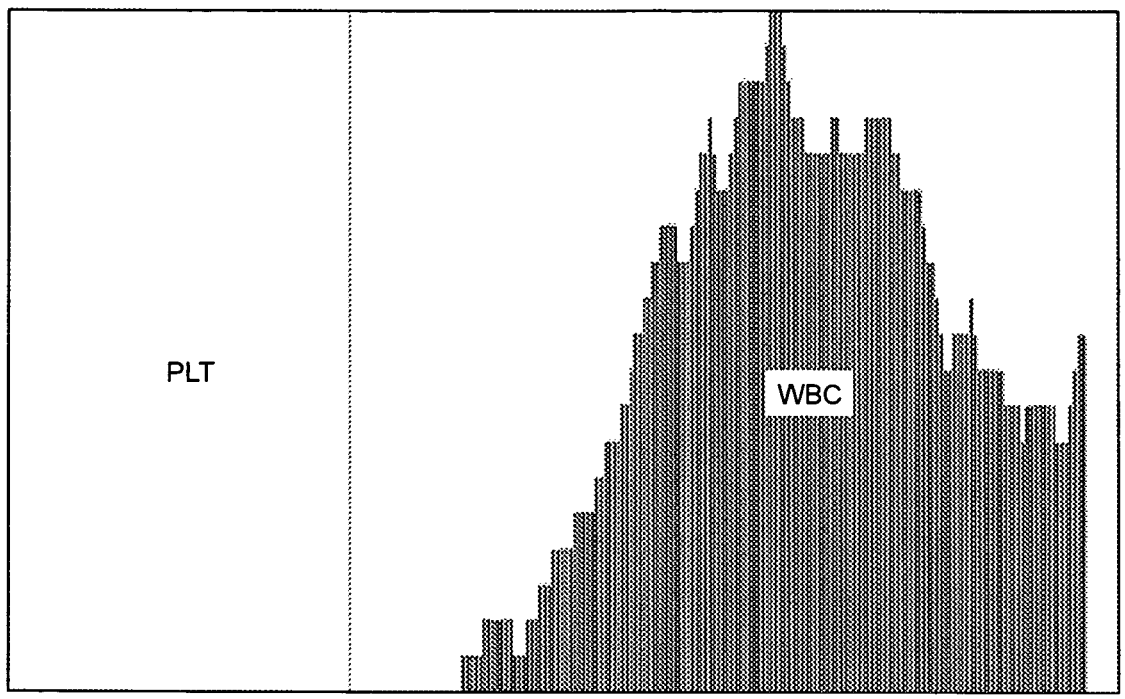
FIG. 6A is a 90° histogram that summarizes the results of FIGS. 5A, 5B, and 5C. The presence of platelet clumps is not apparent.
Figure 6B:
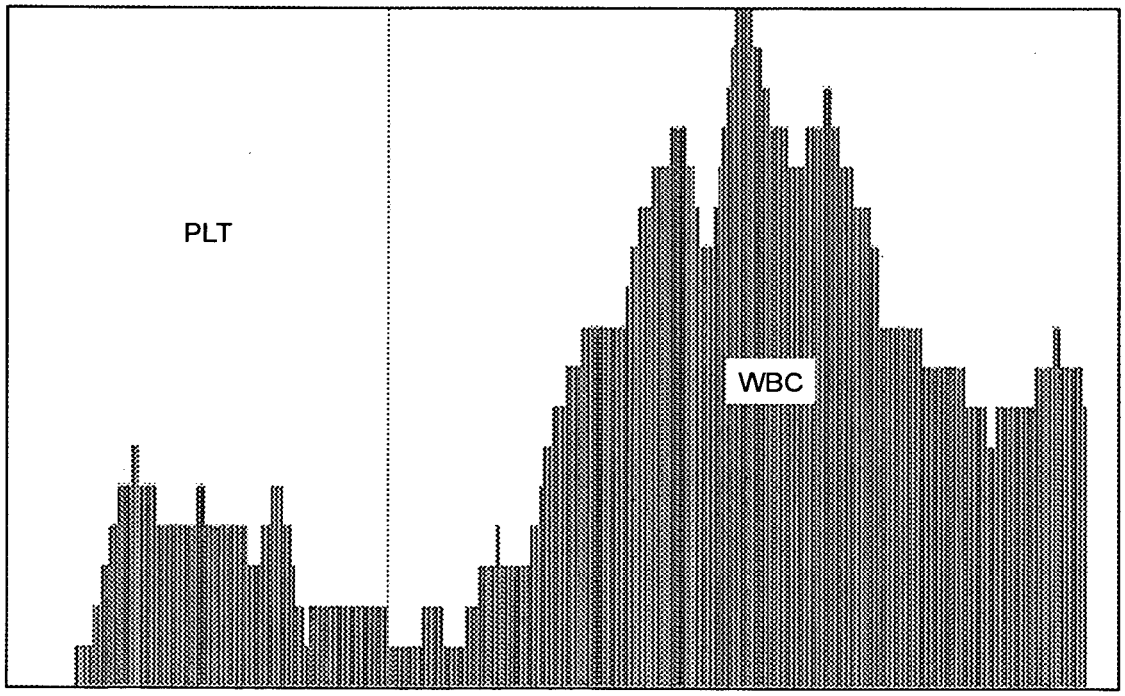
FIG. 6B is a 90° histogram that summarizes the results of FIGS. 5D, 5E, and 5F. The presence of platelet clumps is apparent.

The 90° histogram in FIG. 6A summarizes the results of FIGS. 5B and 5C. The 90° histogram in FIG. 6B summarizes the results of FIGS. 5E and 5F. In FIG. 6A, it can be seen that there is a non-measurable frequency of events to the left of the vertical line and a high frequency of events to the right of the vertical line. The events to the right of the vertical line in FIG. 6A represent the frequency of white blood cell events; the events to the left of the vertical line in FIG. 6A represent the possibility of platelet clump events. In FIG. 6B, it can be seen that there is a measurable frequency, i.e., a moderately high frequency, of events to the left of the vertical line and a high frequency of events to the right of the vertical line. The events to the right of the vertical line in FIG. 6B represent the frequency of white blood cell events; the events to the left of the vertical line in FIG. 6B represent the possibility of platelet clump events.

The 90° detector is used to measure the mismatch of refractive index between the solution outside the cell and inside the cell. Because platelet clumps only have one refractive index (no cell structure) the 90° measurement is low compared with the white blood cell population.

EXAMPLE 7

Figure 7:
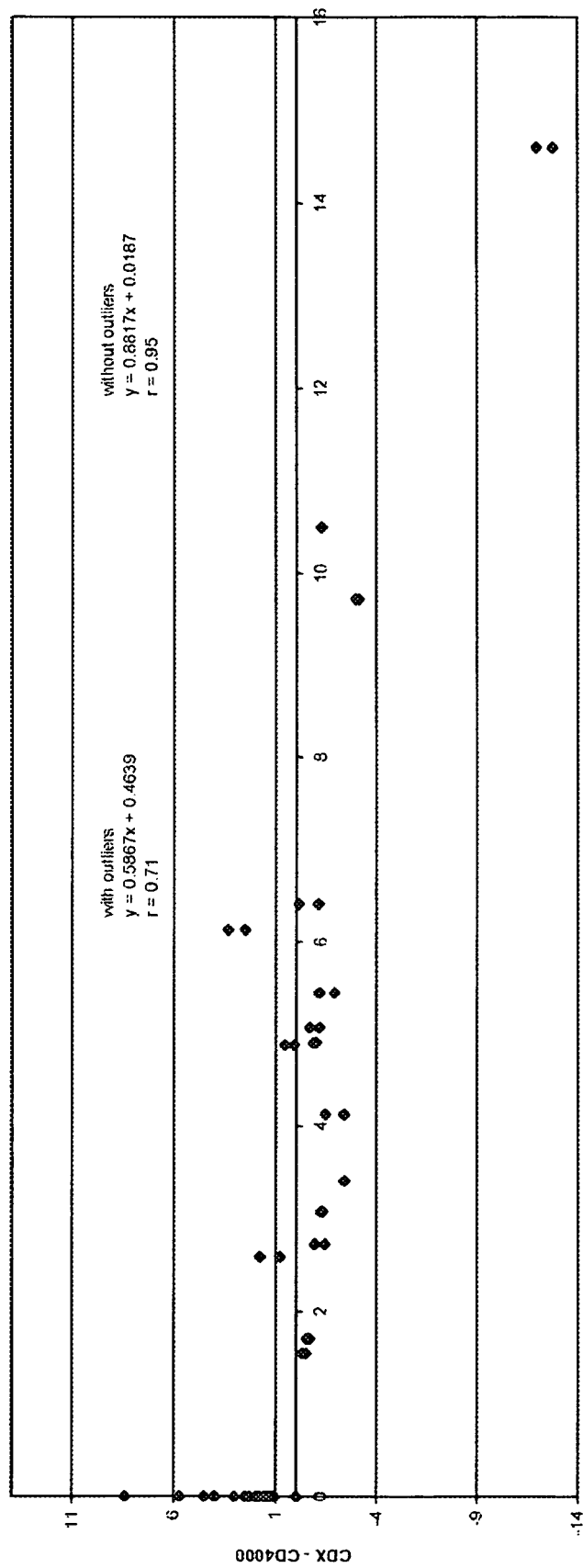
FIG. 7 is a graph that compares the accuracy of the method described herein against the nucleated red blood cell count of the CELL-DYN® 4000 hematology analyzer.

FIG. 7 is a graph that shows the accuracy of the method described herein against the CELL-DYN® 4000 instrument. It can be seen that the method described herein compares very well to the results of the CELL-DYN® 4000 instrument with respect to the percentage of nucleated red blood cells. While the CELL-DYN® 4000 instrument is a very effective instrument, the cost of running that instrument is high, and the CELL-DYN® 4000 instrument is complex. The CELL-DYN® 4000 instrument uses an expensive dye, an expensive complicated lyse reagent, and an expensive light source. These costly components are important for determining white blood cell differential, the white blood cell count, and the nucleated red blood cell count at the same time. The method described herein does not attempt to provide a white blood cell differential. The method described herein provides a more reportable white blood cell result and nucleated red blood cell result, because the method is capable of eliminating various sources of interferences, namely, hypotonically resistant red blood cells, lipids, and platelets clumps. At the same time, samples containing fragile white blood cells are counted accurately. The method of this invention identifies nucleated red blood cells at a concentration of less than 10 nucleated red blood cells per 100 white blood cells, as can be seen from the outlier examples. The method described herein is less costly to implement and perform on account of the lower cost of the light source and reagents that can be used with the method. The CELL-DYN® 4000 instrument currently uses a relatively expensive blue Argon laser. The reagents for the CELL-DYN® 4000 instrument involve two lyse components and propidium iodide dye, which leads to greatly complexity and expense of manufacture, and, consequently, greater expense to the user.

In the bias plot shown in FIG. 7, the vertical axis represents the difference between nucleated red blood cells determined by the algorithm described herein and the nucleated red blood cells determined by the CELL-DYN® 4000 instrument. The data represent the number of nucleated red blood cells per 100 white blood cells. The date involved 106 specimens tested in duplicate, 26 in-house, 80 abnormal with 34 positive nucleated red blood cell counts and 6 fragile lymphocyte counts. From the plot, it can be seen that there is a low outlier. From the plot, it can also be seen that there are numerous false positive test results. The outlier and the false positive test results will be discussed in EXAMPLES 8 and 9.

EXAMPLE 8

Figure 8A:
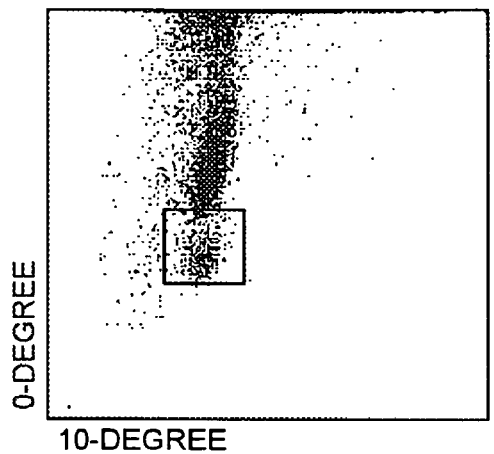
FIG. 8A is a 10°/0° scatter plot that illustrates a low outlier, i.e., an outlier at the right end of FIG. 7.
Figure 8B:
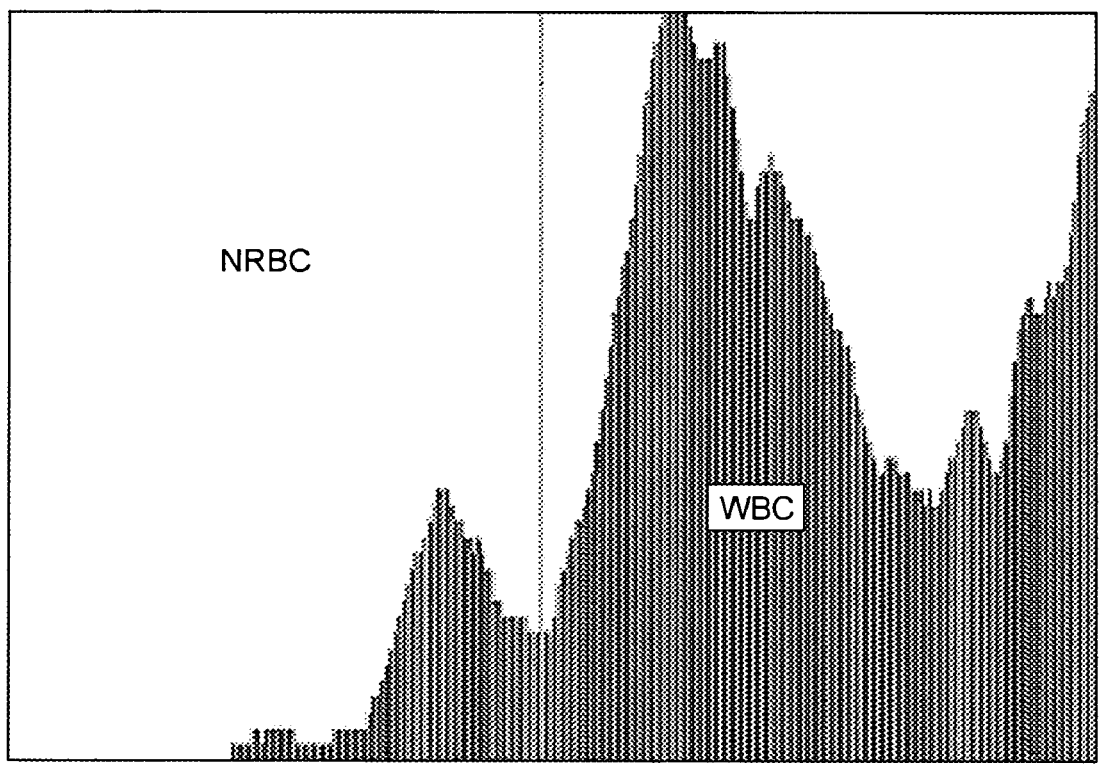
FIG. 8B is a 0° histogram that summarizes the results of FIG. 8A.

This example involves a discussion of the low outlier shown in FIG. 7. FIG. 8A is a scatter plot showing 0° scatter versus 10° scatter, the portion enclosed by the rectangular box includes a significant number of nucleated red blood cell events. The portion above the rectangular box in FIG. 8A includes white blood cell events. In FIG. 8B, it can be seen that there is a measurable frequency, i.e., a moderately high frequency, of events to the left of the vertical line and a high frequency of events to the right of the vertical line. The events to the right of the vertical line in FIG. 8B represent the frequency of white blood cell events; the events to the left of the vertical line in FIG. 8B represent the possibility of nucleated red blood cell events.

EXAMPLE 9

Figure 9A:
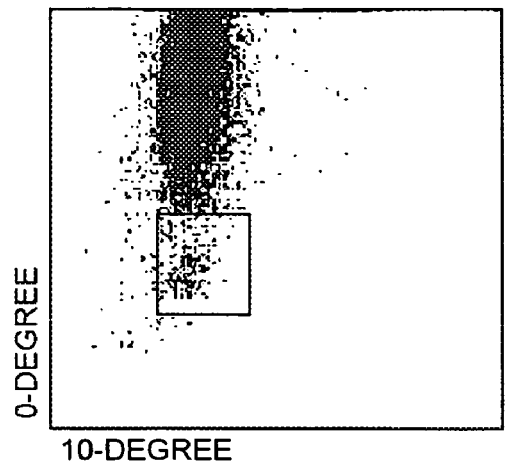
FIG. 9A is a 10°/0° scatter plot that illustrates a false positive or false negative, i.e., results at the left end of FIG. 7.
Figure 9B:
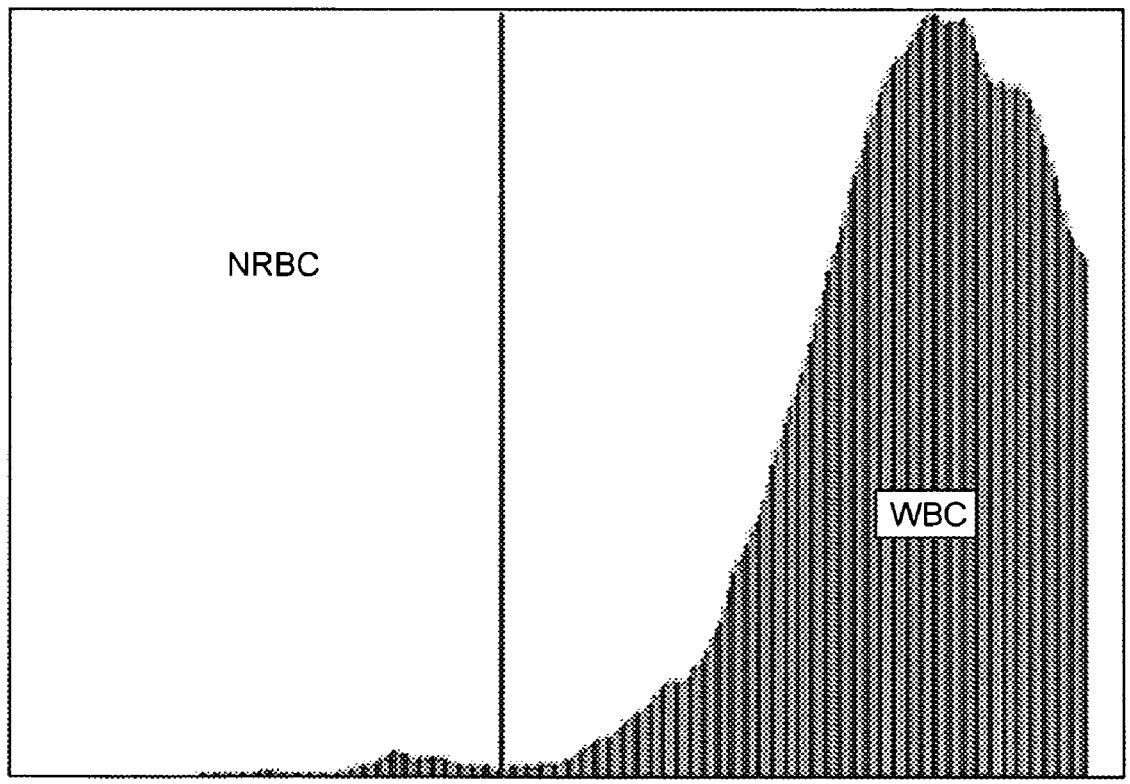
FIG. 9B is a 0° histogram that summarizes the results of FIG. 9A.
Figure 10A:
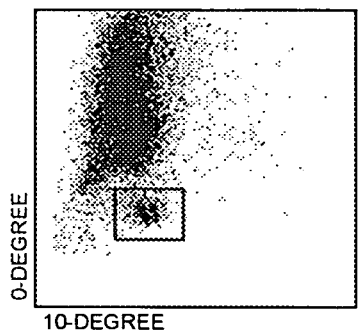
FIGS. 10A, 10B, 10C, 10D, 10E, 10F, and 10G are 10°/0° scatter plots that illustrate a range of abnormal examples, i.e., 1/100 to 162/100 nucleated red blood cells per white blood cells. The boxes indicate where the algorithm searches for the nucleated red blood cells.
Figure 10B:
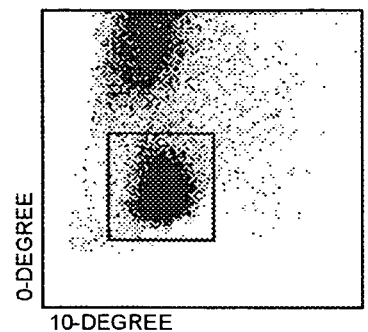
Figure 10C:
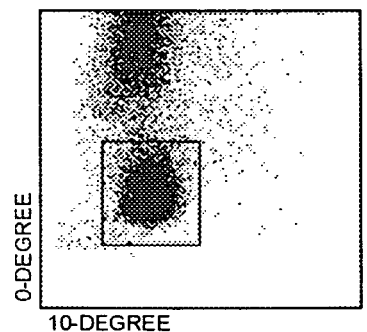
Figure 10D:
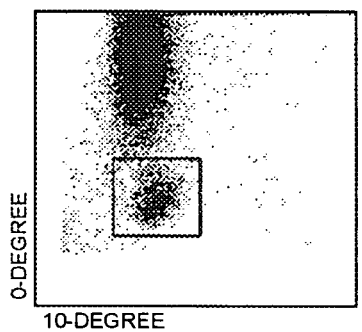
Figure 10E:
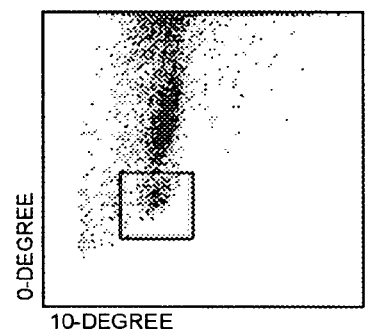
Figure 10F:
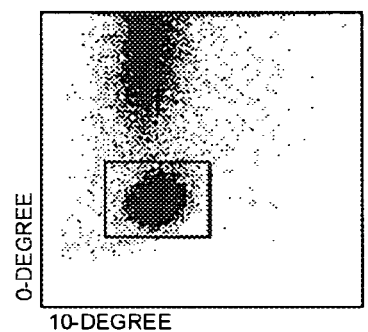
Figure 10G:
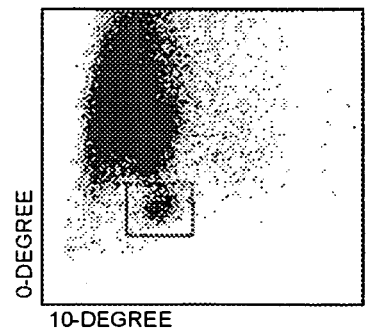
Figure 11:
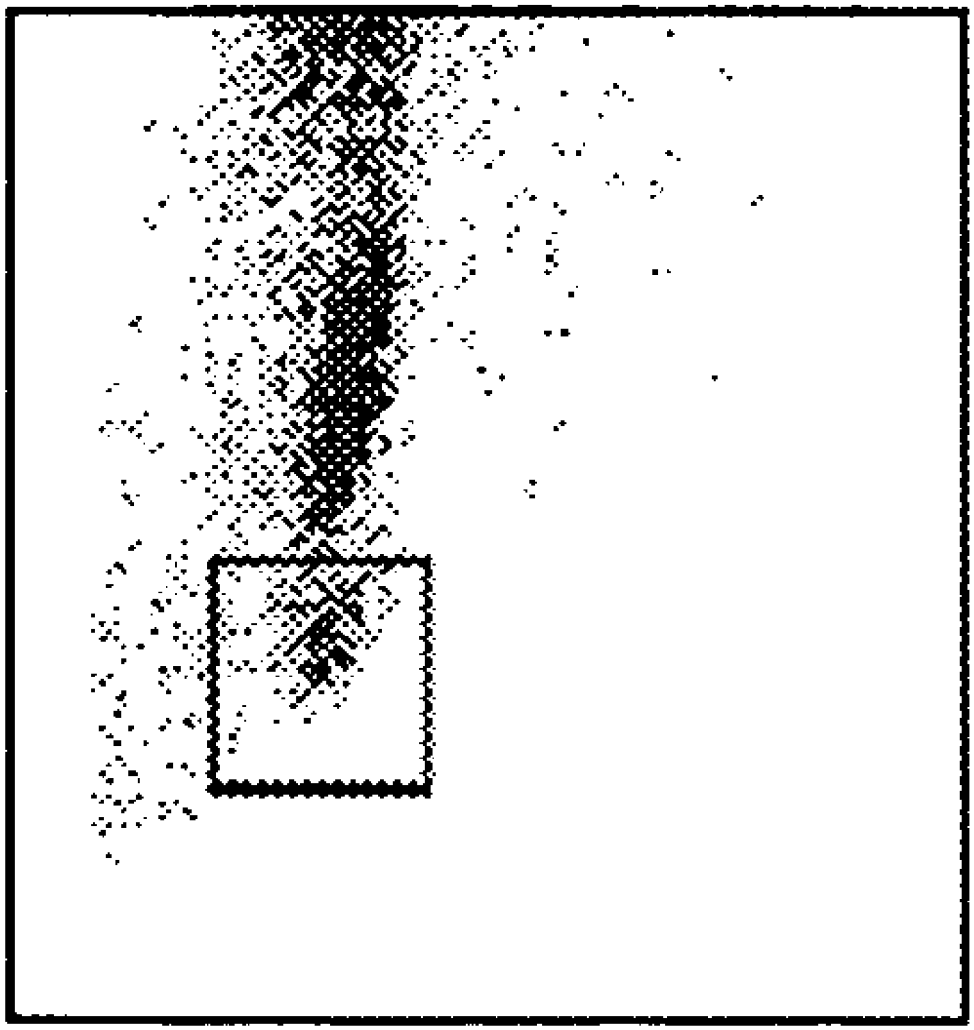
FIG. 11 is a scatter plot that illustrates an abnormal example commonly missed on account of sickle cell interference.

This example involves a discussion of the false positive outliers shown in FIG. 7. One sample is discussed in this example. In FIG. 9A, in the scatter plot showing 0° scatter versus 10° scatter, the portion enclosed by the rectangular box includes a significant number of nucleated red blood cell events. The portion above the rectangular box in FIG. 9A includes a significant number of white blood cell events. In FIG. 9B, it can be seen that there is a measurable frequency, i.e., a moderately high frequency, of events to the left of the vertical line and a high frequency of events to the right of the vertical line. The events to the right of the vertical line in FIG. 9B represent the frequency of white blood cell events; the events to the left of the vertical line in FIG. 9B represent the frequency of nucleated red blood cell events. FIGS. 9A and 9B show that these samples indeed contain nucleated red blood cells.

EXAMPLE 10

This example shows a series of scatter plots that illustrate a range of abnormal examples where nucleated red blood cells are present. The scatter plots show 0° scatter versus 10° scatter. In FIGS. 10A through 10G, inclusive, the blood samples exhibit a range from about 1 to about 162 nucleated red blood cells per 100 white blood cells.

EXAMPLE 11

This example shows a scatter plot that illustrates an abnormal example commonly missed on account of sickle cell interference. The scatter plots show 0° scatter versus 10° scatter. The example shows that the method of this invention can detect nucleated red blood cells in the presence of interfering cells.

EXAMPLE 12

Figures 12A, 12B, 12C:
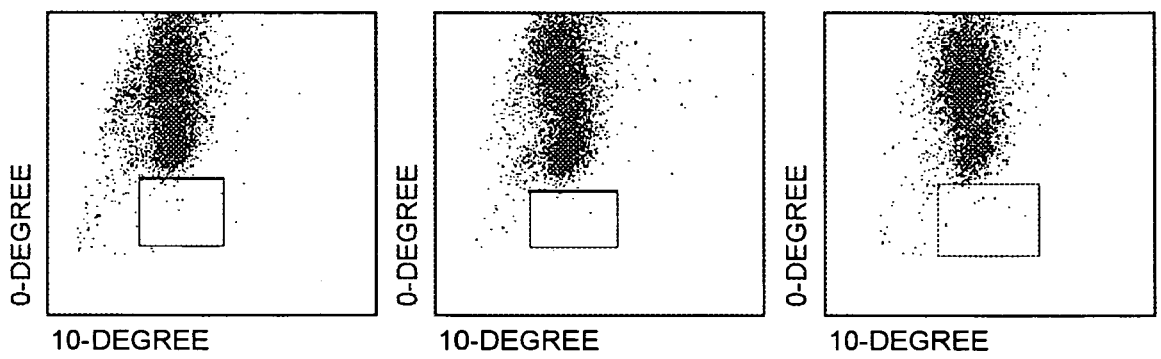
FIGS. 12A, 12B, and 12C are 10°/0° scatter plots that illustrate three normal examples. The boxes indicate where the algorithm searches for the nucleated red blood cells.

This example shows a series of scatter plots that illustrate a range of normal examples of true negatives of nucleated red blood cells. The scatter plots show 0° scatter versus 10° scatter. The rectangular boxes in FIGS. 12A, 12B, and 12C show where the algorithm described herein would search for nucleated red blood cells.

EXAMPLE 13

Figures 13A, 13B, 13C:
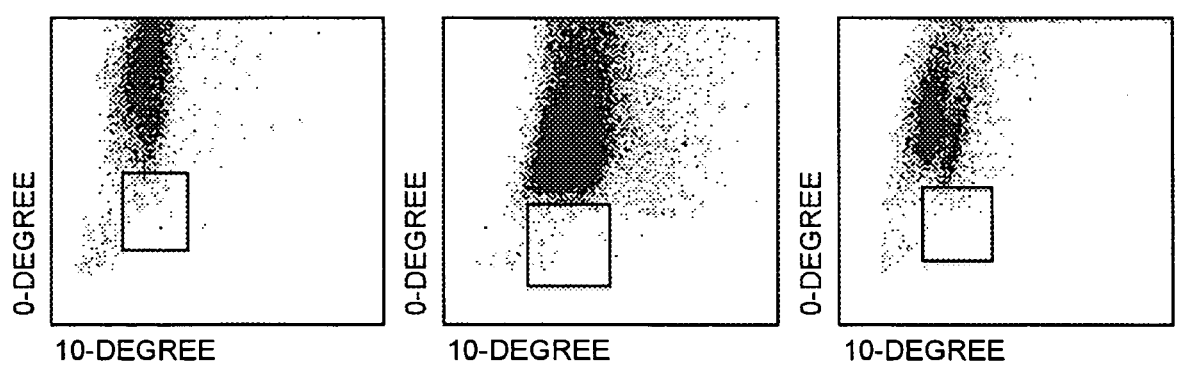
FIGS. 13A, 13B, and 13C are 10°/0° scatter plots that illustrate examples having less than 1/100 nucleated red blood cells per white blood cell. The boxes indicate where the algorithm searches for the nucleated red blood cells.

This example shows a series of scatter plots that illustrate a range of samples of fragile white blood cells. Fragile white blood cells present a challenge to current technology, because fragile white blood cell events resemble nucleated red blood cell events occupying the same scatter space. The scatter plots show 0° scatter versus 10° scatter. The rectangular boxes in FIGS. 13A, 13B, and 13C show where the algorithm described herein would search for nucleated red blood cells. In each blood sample, the events enclosed by the rectangular boxes indicate that there is less than one nucleated red blood cell per 100 white blood cells.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for enumeration of nucleated red blood cells and total white blood cells from the same sample of blood comprising the steps of:
    (a) providing a lysed sample of whole blood;
    (b) subjecting the lysed sample to a multi-scattering depolarizing flow cytometer;
    (c) removing depolarizing interference by using data collected by 90° depolarized scatter and 0° scatter detectors;
    (d) differentiating (i) nucleated red blood cells and noise from (ii) white blood cells in the absence of depolarizing interference, wherein white blood cells are differentiated from noise and nucleated red blood cells by using data collected by 0° scatter and 10° scatter detectors;
    (e) differentiating (i) nucleated red blood cells from (ii) noise in the absence of depolarizing interference and white blood cells, wherein noise is differentiated from nucleated red blood cells by using data collected by 0° scatter and 10° scatter detectors;
    (f) differentiating (i) possible platelet clumps from (ii) white blood cells, wherein possible platelet clumps are differentiated from white blood cells by using data collected by 90° scatter detector,
    and (g) counting nucleated red blood cells and total white blood cells in the lysed sample of whole blood without providing a white blood cell differential analysis.

2. The method of claim 1, wherein depolarizing interference comprises interference from lipids.

3. A method for enumeration of nucleated red blood cells and total white blood cells from the same sample of blood comprising the steps of:
    (a) providing a lysed sample of whole blood;
    (b) subjecting the lysed sample to a multi-scattering depolarizing flow cytometer;
    (c) removing depolarizing interference;
    (d) differentiating (i) nucleated red blood cells and noise from (ii) white blood cells in the absence of depolarizing interference;
    (e) differentiating (i) nucleated red blood cells from (ii) noise in the absence of depolarizing interference and white blood cells;
    (f) differentiating (i) possible platelet clumps from (ii) white blood cells,
    and (g) counting nucleated red blood cells and total white blood cells in the lysed sample of whole blood without providing a white blood cell differential analysis,
    wherein the lysed sample of whole blood was lysed by means of a diluent and a lyse reagent, the ratio of the lyse reagent to the diluent ranging from about 1:3 to about 1:8.

4. The method of claim 3, wherein depolarizing interference comprises interference from lipids.

5. A method for enumeration of nucleated red blood cells and total white blood cells from the same sample of blood comprising the steps of:
    (a) providing a lysed sample of whole blood;
    (b) subjecting the lysed sample to a multi-scattering depolarizing flow cytometer;
    (c) removing depolarizing interference;
    (d) differentiating (i) nucleated red blood cells and noise from (ii) white blood cells in the absence of depolarizing interference;
    (e) differentiating (i) nucleated red blood cells from (ii) noise in the absence of depolarizing interference and white blood cells;
    (f) differentiating (i) possible platelet clumps from (ii) white blood cells,
    and (g) counting nucleated red blood cells and total white blood cells in the lysed sample of whole blood without providing a white blood cell differential analysis,
    wherein the lysed sample of whole blood was lysed by means of a diluent and a lyse reagent, wherein the lyse reagent comprises at least one quaternary ammonium salt and a hydroxylamine salt, the ratio of the lyse reagent to the diluent ranging from about 1:3 to about 1:8.

6. The method of claim 5, wherein depolarizing interference comprises interference from lipids.

7. A method for enumeration of nucleated red blood cells and total white blood cells from the same sample of blood comprising the steps of:
   (a) providing a lysed sample of whole blood;
   (b) subjecting the lysed sample to a multi-scattering depolarizing flow cytometer;
   (c) removing depolarizing interference by using data collected by 90° depolarized scatter and 0° scatter detectors;
   (d) differentiating (i) nucleated red blood cells and noise from (ii) white blood cells in the absence of depolarizing interference, wherein white blood cells are differentiated from noise and nucleated red blood cells by using data collected by 0° scatter and 10° scatter detectors;
   (e) differentiating (i) nucleated red blood cells from (ii) noise in the absence of depolarizing interference and white blood cells, wherein noise is differentiated from nucleated red blood cells by using data collected by 0° scatter and 10° scatter detectors;
   (f) differentiating (i) possible platelet clumps from (ii) white blood cells, wherein possible platelet clumps are differentiated from white blood cells by using data collected by 90° scatter detector,
   and (g) counting nucleated red blood cells and total white blood cells in the lysed sample of whole blood without providing a white blood cell differential analysis,
   wherein the lysed sample of whole blood was lysed by means of a diluent and a lyse reagent, wherein the lyse reagent comprises at least one quaternary ammonium salt and a hydroxylamine salt, the ratio of the lyse reagent to the diluent ranging from about 1:3 to about 1:8.

8. The method of claim 7, wherein depolarizing interference comprises interference from lipids.

* * * * *